(12) United States Patent
Tejedor Vinent et al.

(10) Patent No.: US 7,531,684 B2
(45) Date of Patent: May 12, 2009

(54) PROCESS FOR MAKING AMINOALKYLPHENYL CARBAMATES AND INTERMEDIATES THEREFOR

(75) Inventors: Henar Tejedor Vinent, Lent (NL); Arjanne Overeem, Beuningen (NL); Lambertus Thijs, Wijchen (NL)

(73) Assignee: Synthon BV, Nijmegen (NL)

( * ) Notice: Subject to any disclaimer, the term of this patent is extended or adjusted under 35 U.S.C. 154(b) by 0 days.

(21) Appl. No.: 11/863,779

(22) Filed: Sep. 28, 2007

(65) Prior Publication Data

US 2008/0154057 A1    Jun. 26, 2008

Related U.S. Application Data

(60) Provisional application No. 60/827,613, filed on Sep. 29, 2006.

(51) Int. Cl.
*C07C 269/00* (2006.01)
*C07C 271/00* (2006.01)
(52) U.S. Cl. .......................... 560/33; 560/115; 560/136; 560/163
(58) Field of Classification Search .................. 560/32, 560/115, 136, 163, 33
See application file for complete search history.

(56) References Cited

U.S. PATENT DOCUMENTS 4,948,807 A    8/1990   Rosin et al.
5,602,176 A    2/1997   Enz
2005/0096387 A1    5/2005   Verheijen et al.

FOREIGN PATENT DOCUMENTS

| CN | 1486973 | 4/2004 |
|----|---------|--------|
| EP | 0 193 926 B1 | 11/1990 |
| GB | 2 203 040 A | 10/1988 |
| WO | WO 03/101917 A2 | 12/2003 |
| WO | WO 2004/037771 A1 | 5/2004 |
| WO | WO 2006/048720 A1 | 5/2006 |

*Primary Examiner*—Sikarl A Witherspoon
(74) *Attorney, Agent, or Firm*—Mark R. Buscher

(57) ABSTRACT

A process for making aminoalkylphenyl carbamates, especially rivastigmine, can use less severe conditions using bis(p-nitrophenyl)carbonate (IX) as a phenol activator compound.

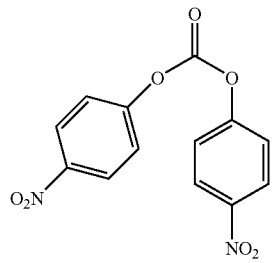

(IX)

20 Claims, No Drawings

PROCESS FOR MAKING AMINOALKYLPHENYL CARBAMATES AND INTERMEDIATES THEREFOR

The present application claims the benefit of priority under 35 U.S.C. § 119(e) from U.S. provisional application Ser. No. 60/827,613, filed Sep. 29, 2006, the entire contents of which are incorporated herein by reference.

BACKGROUND OF THE INVENTION

The present invention provides an improved process for making [3-[α-(dimethylamino)ethyl]phenyl]-N-methylethylcarbamate, a useful pharmaceutically active agent.

Rivastigmine is a generic name for the compound (S)-[3-[α-(Dimethylamino)-ethyl]phenyl]-N-methylethylcarbamate of the formula (Ib):

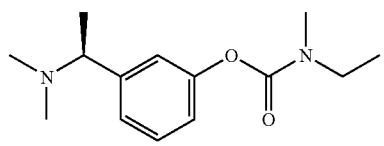

More generally, rivastigmine is the (S)-enantiomer of a compound of general formula (I), wherein the dotted line indicates that this carbon-carbon bond is attached to the asymmetric carbon and the compound of formula (I) may exist as a racemate or as an enantiomer.

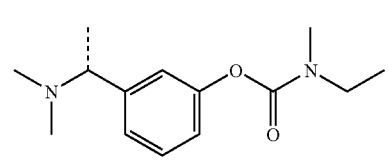

Rivastigmine (Ib) is a pharmaceutically active compound that acts as a reversible, brain-selective acetylcholinesterase inhibitor. In existing medicinal products, it is marketed as a salt with L-tartaric acid-rivastigmine hydrogentartrate. Rivastigmine hydrogentartrate is indicated for the symptomatic treatment of mild to moderately severe Alzheimer disease.

The compound of formula (I) has been disclosed in EPB 193,926 and the U.S. Pat. No. 4,948,807. Rivastigmine hydrogentartrate was specifically disclosed in U.S. Pat. No. 5,602,176.

The compound of formula (I) is a phenylcarbamate, i.e., its molecule is formed by a phenolic moiety A linked by a carbonyl bridge C to an aminic moiety B as shown in the schematic figure below:

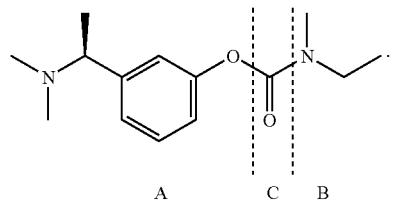

Accordingly, the known processes for making compounds of formula (I), including rivastigmine, generally employ the aminophenol compound (II) and ethylmethylamine (III) as starting materials:

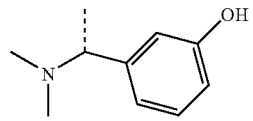

with various ways of constructing the carbonyl linking bridge.

As in the compound (I), the compound (II) has one asymmetric carbon (illustrated by the dotted line in the figure (II)) and may be employed in the synthesis of rivastigmine as the racemate (IIa) or as a single enantiomer, preferably the S-enantiomer (IIb).

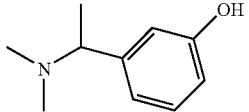

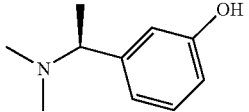

In the first case, racemic compound (I-R) is produced, which can be resolved into its enantiomers to yield rivastigmine. In the latter case, rivastigmine is produced directly. The compound (IIb) is generally obtainable by the resolution of the compound (IIa) into enantiomers. Schematically, the whole process may be depicted as follows:

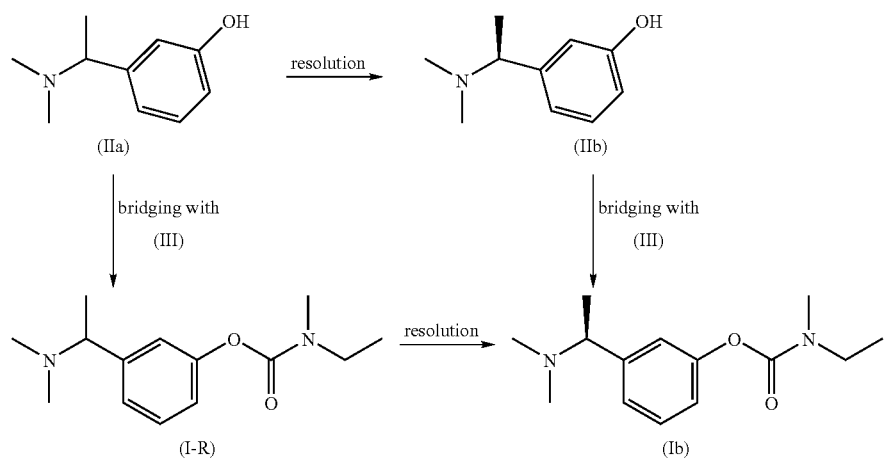

The original process employed the racemic compound (IIa), yielding the racemate (I-R). The resolution of the (I-R) into enantiomers as well as the isolation of the (S)-enantiomer as a hydrogentartrate salt has been disclosed in GB 2203040.

This process has been improved in WO 2004-037771, wherein it was found that the racemic (IIa) may be replaced by the enantiomerically pure compound, particularly the (S)-enantiomer (IIb). No racemization occurs during the subsequent bridge-forming reaction and the desired rivastigmine (Ib) may thus be prepared without the resolution in the last step. A similar process has been disclosed in CN 1486973.

Two general synthetic concepts are known for building up the bridge (C) between the compounds (II) and (III) to form the desired carbamoyl ester.

The first concept is based on the activation of the amine (III) before the reaction with the phenol. The activated intermediate may be isolated and then it reacts with the aminophenol (II). In EPB 193926, the activated intermediate (the bridge-forming reagent) is a carbamoyl halide of the formula (IV):

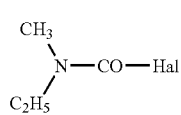

(IV)

which is formed by the reaction of compound (III) with a phosgene reagent. The condensation reaction with compound (II) needs an excess of this carcinogenic substance and requires the presence of sodium hydride as a base. In another possibility, the amine (III) may be converted into an isocyanate, which then reacts with compound (II).

In WO 03-101917, the bridge-forming reagent is a carbamoyl ester, particularly the p-nitro phenyl carbamate of the formula (V).

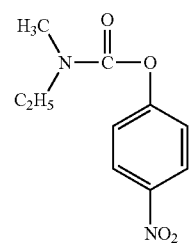

(V)

The reported advantage is that the use of compound (V) does not require the use of NaH for the condensation reaction with compound (II), allowing more common bases to be used. Another reported advantage is that the bridge-forming reagent (V) is less hazardous and more user-friendly. However, the reaction using compound (V) requires high temperatures and long reaction time (100° C., 35-40 hours). The carbamate (V) must be synthetized in an extra reaction step involving the ethylmethyl amine (III) and p-nitrophenylchloroformate (VI).

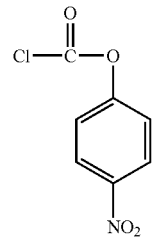

(VI)

Conversely, the second concept is based on the activation of the phenol group in (II) by an activation agent; typically forming an intermediate of general formula (VII).

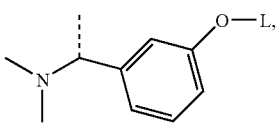

The intermediate (VII) is reacted with the amine (III), wherein L is a suitable leaving group, to form the compound (I). This concept was generally discussed in US 2005/0096387 for compounds similar to rivastigmine and was actually used for the synthesis of rivastigmine in WO 2006-048720, wherein the activation agent "of choice" is carbonyldiimidazole (VIII).

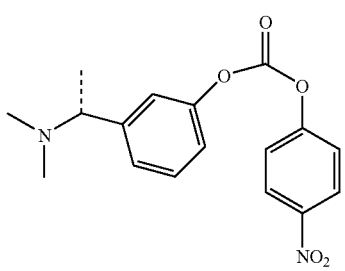

The reaction intermediate (VII) may be produced in situ and may react with the amine (III) without a need of its isolation, which is an advantage over the first concept. The reported reaction conditions for forming the intermediate (VII) by using carbonyldiimidazole (VIII) are disadvantageous (e.g., long reaction time and high temperatures).

WO 2006-048720 also provides for an alternative within this second concept, where the phenol activation agent may be p-nitrophenylchloroformate (VI); also mentioned above as an amine activation agent (see pg. 6, line 29-30, of WO 2006-048720). If one were to apply this activation agent to the corresponding phenol compound, it appears that the active intermediate (VII) could be represented as the compound (VII-1).

It has been discovered during the research leading to the present invention that the reaction conditions for activating the compound (II) with p-nitrophenylchloroformate (VI) are disadvantageous, including the need to use very low temperatures (e.g., less than −40° C.) in order to obtain the product with good yield and purity (see Comparative example 1 hereinafter).

Accordingly, there is a need to provide a simple process for making the compound of formula (I), particularly rivastigmine of the formula (Ib) and/or its racemic analogue (Ia), that can avoid extreme reagents and/or extreme conditions.

SUMMARY OF THE INVENTION

The present invention relates to the use of a bis(p-nitrophenyl)carbonate in forming aminoalkylphenyl carbamates, especially rivastigmine. Accordingly, a first aspect of the invention relates to a process, which comprises:

(a) reacting a compound of formula (II)

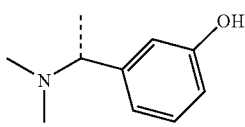

with bis(p-nitrophenyl)carbonate of formula (IX)

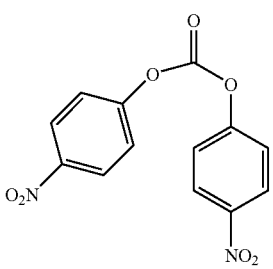

to form an intermediate and (b) reacting the intermediate with ethylmethylamine of formula (III)

to form a compound of formula (I)

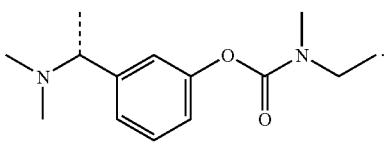

For clarity, the dashed line shown for the carbon-carbon bond on the asymmetrical carbon atom indicates that individual enantiomers as well as mixtures are included within the scope of formulae (I) and (II). Step (a) can generally be conducted at a temperature between −20 to 50° C., usually in an inert solvent. The intermediate formed by step (a) and used in the reaction of step (b) is believed to be a compound of formula (VII-1).

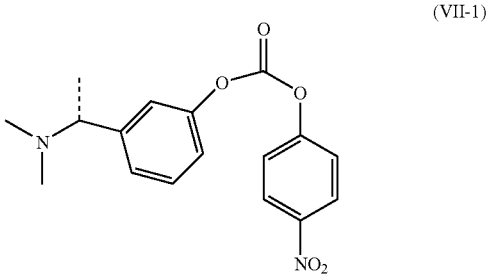

With or preferably without isolation, the intermediate is reacted with ethylmethylamine of the formula (III) to form a compound of formula (I).

The compound of formula (I) may be isolated from the reaction mixture and/or, provided that the compound of formula (I) is a racemate, resolved into enantiomers and/or isolated as an acid addition salt, most preferably as a hydrogentartrate salt. The process can thus provide rivastigmine as a free base or as an acid addition salt, preferably the hydrogentartrate salt.

DETAILED DESCRIPTION

The starting material of the process is a compound of general formula (II), which comprises both the racemic compound of the formula (IIa), any single enantiomer thereof, particularly the (S) enantiomer of the formula (IIb), and mixtures of both enantiomers.

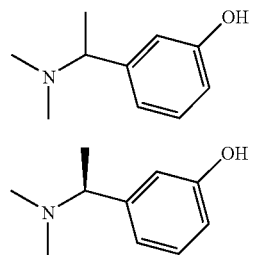

Any of the specific compounds of the general formula (II) are useful. They may be obtained by methods and processes known in the art and discussed above.

The process for making the compound (I) involves two chemical reactions. Accordingly, it will be described as a two step process. While the steps are normally run separately, that is consecutively, the process may nonetheless be conveniently performed in a one pot arrangement as well, e.g. as a 'one pot process' without isolation of the intermediate product.

In the first step of the process, the compound of formula (II), particularly the racemate (IIa) and/or the (S)-enantiomer of the formula (IIb), reacts with bis(p-nitrophenyl)carbonate of the formula (IX). The reaction conditions are not particularly limited but typically comprise reacting both compounds at a temperature of between −20 to 50° C., most preferably between 0 and 30° C., in an organic solvent and, advantageously but not necessarily, under the presence of a base. Concerning the temperatures, higher temperatures than those as above are less suitable as side products may be formed to a greater extent as compared to the preferred temperatures, while lower temperatures are less suitable as specific cooling equipment and extra energy costs are generally necessary for industrial production and the reaction time can be quite long. Concerning the organic solvent, any inert solvent may be employed in principal, but solvents with higher solubility for the reactants and the products are preferred because they enable better control of the reaction. For instance, the solvent may be an C1-C10 ether (e.g. methyl tert. butyl ether), a C5-C8 cyclic ether (e.g. tetrahydrofuran) a C2-C10 aliphatic ester (e.g. ethyl acetate), a C2-C8 aliphatic nitrile (e.g. acetonitrile), an amide (e.g. dimethylformamide), a sulfoxide (e.g. dimethyl sulfoxide), a ketone (e.g. acetone), a C5-C10 hydrocarbon (e.g. hexane or toluene), a C1-C8.chlorinated hydrocarbon (e.g. chloroform or dichloromethane), and/or mixtures thereof. Protic solvents such as alcohols or basic solvents (such as pyridine) are not suitable as they may react and are thus not inert. The base, is generally an organic base, preferably a tertiary amine, e.g. triethylamine or pyridine. More than one molar equivalent of the base is generally used, if a base is used at all.

The reaction time depends in part on the temperature and is generally less than 10 hours. In an advantageous mode, the course of the reaction is monitored by a suitable analytical method, for instance by HPLC and/or by TLC, and the second step of the reaction process does not start until the first reaction step is essentially completed, i.e. more than 95%, preferably more than 98% of the starting material (II) has been converted/consumed.

The product of the first reaction step is believed to be the carbonate intermediate of the formula (VII-1).

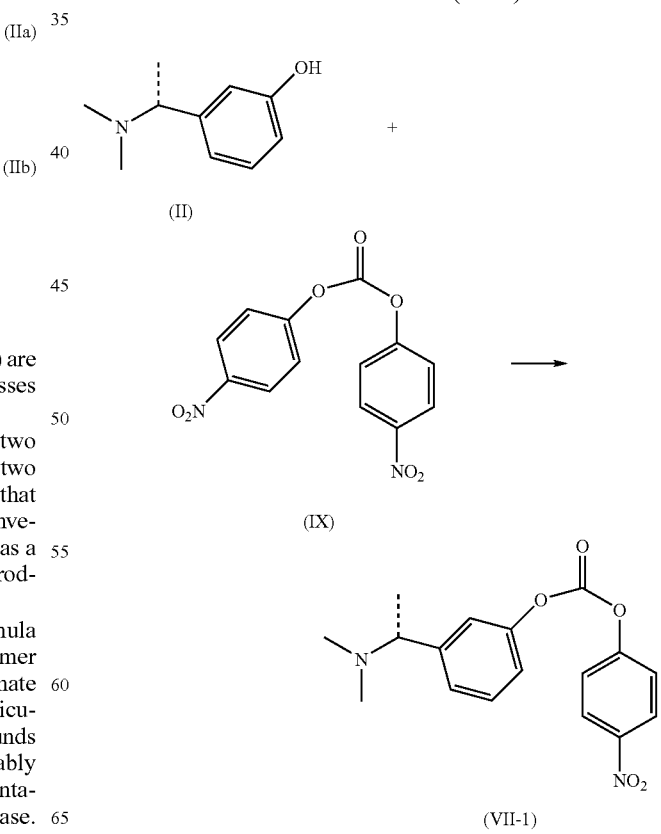

Dependent on the starting material, one may produce the racemate of the formula (VII-1a), the single enantiomer, preferably the S-enantiomer (VII-1 b), or a mixture of both enantiomers.

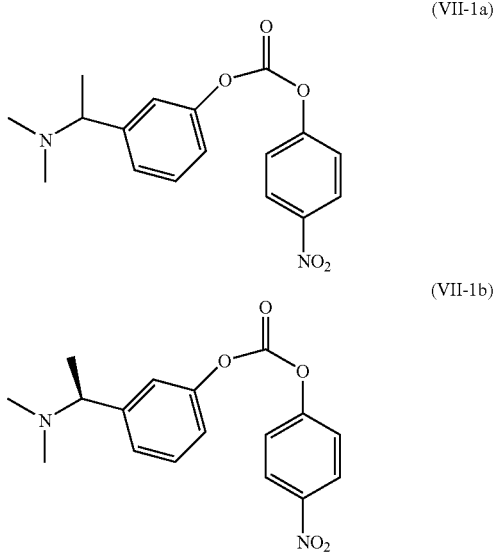

The optical purity of the intermediate (VII-1) is essentially identical with that of the starting material (II). Thus, the racemic (IIa) provides the racemate (VII-1a), the S-enantiomer (IIb) provides the S-enantiomer (VII-1b), etc.

In essence, there is no need to isolate the reaction product (VII-1) from the reaction mixture. Nevertheless, the product is isolatable and may be isolated from the reaction mixture, e.g., with the aim to remove the rest of the unreacted products and to enhance the quality of the final product. One example of a suitable mode of isolation is an extraction process.

In the second step of the process of the invention, the product of the first step, either in the isolated or in the non-isolated state, reacts with the ethylmethylamine of the formula (III). This compound (III) is commercially available.

The reaction conditions of the second step typically comprise contacting both reagents in a suitable inert organic solvent at a temperature of between −20 and 50° C., preferably between 0 and 30° C.

As stated above, it is possible to use the reaction mixture from the first step as the starting material for the reaction with the compound (III) in the second step. Accordingly, the compound (III) can be added, portion wise or at once, as such or dissolved in a solvent, to the reaction mixture of the first step, and the reaction proceeds, typically while stirring the reaction mixture, at the selected temperature. More than 1 equivalent of the amine (III), and preferably more than 2 molar equivalents, are generally added.

If the isolated intermediate (VII-1) from the first step is used, the reaction with (III) in the second step proceeds in the same kind of solvent listed above as useful for the first step. A base, preferably an organic base, may be added to the reaction mixture.

The course of the reaction is monitored by a suitable analytical method, e.g. by HPLC, and the reaction is terminated in the proper time, e.g., when the desired product is formed at a desired quantity, purity, etc.

The product of the second reaction step is the compound of formula (I). Similarly as above, the actual conformation of the product depends on the conformation of the starting material. It was found that no racemization occurs within the second step, so that a single enantiomer of the formula (IIb) provides for the single enantiomer of the compound (I), the compound of formula (Ib), i.e. rivastigmine.

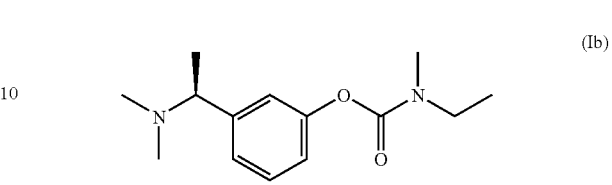

The reaction product (I) from the second step is typically isolated from the reaction mixture. The reaction mixture is first treated with water and the product (I) is isolated from the organic phase. Before isolation, the organic phase may be optionally further purified, e.g., by chromatography or by extraction. The extraction process is preferred. In a suitable mode, the extraction process comprises the extraction of the product (which is an amine) from the organic solvent by acidified water, followed by adjusting the aqueous extract to an alkaline pH and re-extracting the alkaline aqueous solution with an organic solvent. There are no particular limitations on the acid, e.g., hydrochloric acid may be used for the acidification of the water. An alkali, e.g., sodium hydroxide, may be used for adjustment of the pH to alkaline values. Concerning the organic solvent, any water immiscible organic solvent may be used.

The product may be isolated from the solution as the base, e.g. by evaporation of the solvent. In such a case, the product generally appears as an oil. Advantageously, however, the product may be isolated as an acid addition salt, whereby it may appear in a solid state, by adding the suitable acid to the reaction mixture or to the isolated base and precipitating the salt. The acid can be, e.g., hydrochloric acid, and is most preferably L-tartaric acid. In the later case, the hydrogentartrate salt of the product of formula (I) is obtained.

If the starting compound (II) is the racemate (IIa), the product of the process will be the compound of formula (I) as a racemate as well, e.g. formula (Ia).

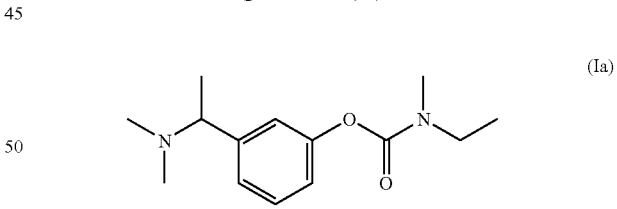

As stated above, the pharmaceutically preferable form of the compound of formula (I) is the S-enantiomer, the rivastigmine of formula (Ib), and particularly the rivastigmine hydrogentartrate. Therefore, if the rivastigmine is to be obtained, the formed racemate (Ia) should be resolved into enantiomers and the desired S-enantiomer (Ib) should be isolated. For clarity, isolation is achieved, vis-à-vis the other enantiomer, if the separation is substantial; typically only small amounts of the R-enantiomer remaining with the S-enantiomer (Ib) such as would be an acceptable amount in a pharmaceutical. The resolution processes are known in the art and employ the treatment of the racemate with a chiral acid. A diastereomeric pair of salts is formed by such treatment, whereby the conditions of formation may be selected such that one of the salts of this pair precipitate from the reaction mixture and the other remains in the solution.

When using the L-tartaric acid as the chiral acid, and, e.g., acetone as the solvent, then rivastigmine L-hydrogentartrate, the most desired salt of rivastigmine, directly precipitates.

If starting with the compound (IIb), rivastigmine (Ib) and particularly rivastigmine L-hydrogentartrate may be obtained in a simple process, which does not require special equipment and uncommon reaction conditions. Advantageously, the process of the invention does not require extremely high or extremely low reaction temperatures as do the corresponding processes of the prior art. The process of the invention provides the desired product in high yield and high purity without racemization. The invention will be further described by way of the following non-limiting examples.

EXAMPLES

Comparative Example 1

Reaction Scheme

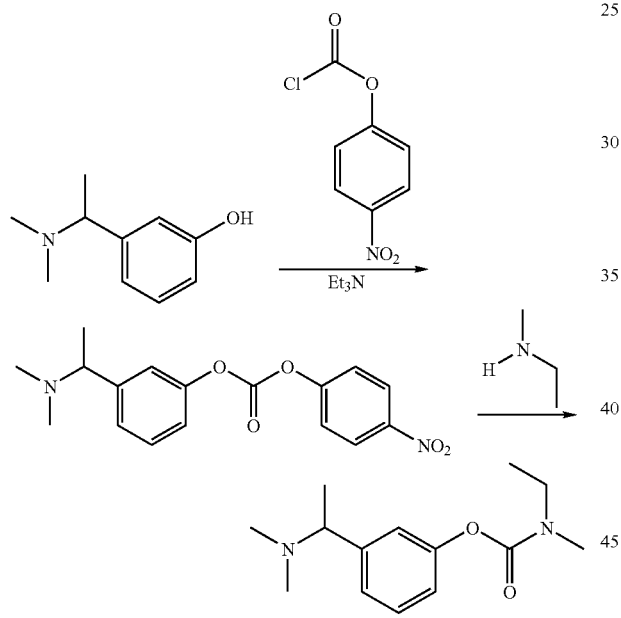

1 g 3-(1-Dimethylamino)ethyl) phenol was dissolved in 20 ml dichloromethane (dried on $CaCl_2$). The solution was cooled to −78° C.

0.92 g Triethylamine was added. A solution of 1.22 g 4-nitrophenyl chloroformate in 5 ml dichloromethane (dried on $CaCl_2$) was added dropwise over 5 minutes. The solution was stirred at −78° C. Reaction progress was monitored by HPLC. After 3 hours at −78° C., HPLC showed that there was still starting material present. A second addition of 0.61 g 4-nitrophenyl chloroformate in 2 ml dichloromethane (dried on $CaCl_2$) was made. After 30 min at −78°, the starting material was completely converted (acc. to HPLC).

715 mg N-Ethylmethylamine was added and the yellow reaction mixture was allowed to warm slowly to 0° C. The reaction mixture was stirred for 40 hours at 4° C. The reaction mixture was allowed to warm to room temperature and was then washed with 2×20 ml water. The organic phase was concentrated in vacuo. To the resulting yellow oil, 20 ml diethyl ether and 20 ml of a solution of hydrochloric acid (2 M) were added. The 2-phase system was stirred for 15 minutes. The acidic aqueous layer was washed with 20 ml diethyl ether.

20 ml dichloromethane was added to the aqueous layer and a solution of sodium hydroxide (2 M) was added until pH~10-11 was reached. The organic layer was washed with 2×20 ml water, dried ($Na_2SO_4$), filtered and concentrated in vacuo.

| Isolated yield: | 1.4 g (93%), yellow oil |
| --- | --- |
| HPLC: | 97.6% purity |
| $^1$H-NMR: | confirmed the expected structure |

The Comparative example 1 was repeated with the following solvents and first step reaction temperatures with the following results:

TABLE 1

| Exp. code | Solvent | Reaction temperature (° C.) | Isolated yield (%) | Purity according to HPLC |
| --- | --- | --- | --- | --- |
| Comparative Example 2 | $CH_2Cl_2$ | −20 | 68 | 94.4 |
| Comparative Example 3 | $CH_2Cl_2$ | 0-5 | 39 | 93.7 |
| Comparative Example 4 | $CHCl_3$ | −20 | 66 | 94.0 |
| Comparative Example 5 | EtOAc | −20 | 55 | 97.2 |
| Comparative Example 6 | $CH_3CN$ | −20 | 69 | 95.5 |
| Comparative Example 7 | THF | −20 | * | |

* Reaction was stopped after first step, because of bad result obtained.

Accordingly, very low temperatures were needed to obtain high yields, e.g. −78° C. to obtain 93% yield, while merely cold temperatures (e.g., 0-5° C.) produce low yields (e.g. 39%).

Example 1

Synthesis and Isolation of Compound VII-1a without Using (IX)

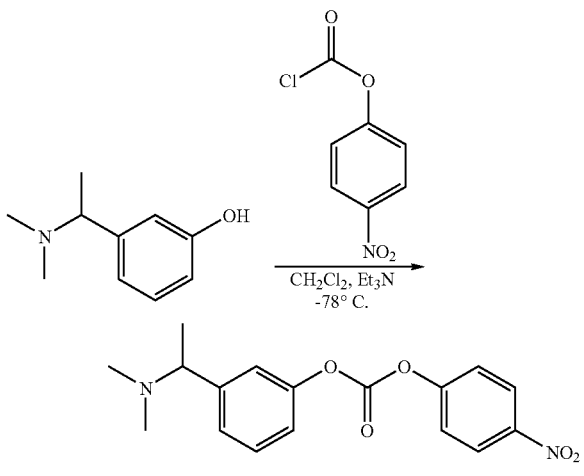

1 g 3-(1-Dimethylamino)ethyl) phenol was dissolved in 20 ml dichloromethane (dried on CaCl$_2$). The solution was cooled to −78° C. 0.92 g triethylamine was added. A solution of 1.22 g 4-nitrophenyl chloroformate in 5 ml dichloromethane (dried on CaCl$_2$) was added dropwise over 5 minutes. The mixture was stirred at −78° C. Reaction progress was monitored with HPLC. After 3 hours at −78° C., the reaction mixture was allowed to warm to ambient temperature and was then washed with 2×20 ml water, dried (Na$_2$SO$_4$), filtered and concentrated in vacuo.

| Isolated yield: | 2.1 g, yellow oil |
| --- | --- |
| HPLC: | 83% purity |
| $^1$H- and $^{13}$C-NMR: | confirmed the expected structure |

Example 2

Synthesis and Isolation of the Compound (VII-1b) Using (IX)

Reaction Scheme:

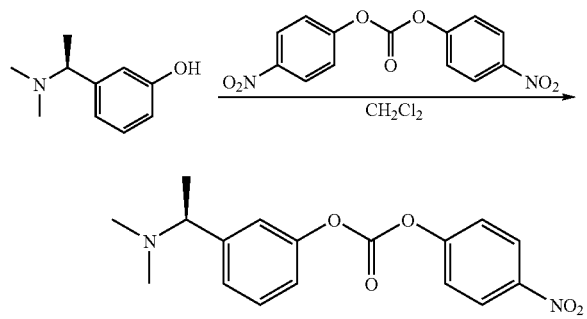

0.5 g (S)-3-(1-(Dimethylamino)ethyl) phenol was dissolved (not completely) in 10 ml dichloromethane (distilled from CaCl$_2$). 1.1 g bis(4-nitrophenyl)carbonate was added. The yellow solution was stirred at ambient temperature. Reaction progress was monitored with HPLC. The reaction mixture was concentrated in vacuo. To the resulting yellow oil, 20 ml diethyl ether and 20 ml of a solution of hydrochloric acid (2 M) were added. The 2-phase system was stirred for 15 minutes. The acidic aqueous layer was washed with 20 ml diethyl ether.

20 ml dichloromethane was added to the aqueous layer and a solution of sodium hydroxide (2 M) was added until pH~12 was reached. The organic layer was washed with 2×20 ml water, dried (Na$_2$SO$_4$), filtered and concentrated in vacuo.

| Isolated yield: | 0.57 g (57%), yellow oil |
| --- | --- |
| HPLC: | 84.2% purity |

Example 3

Synthesis of Rivastigmine from the Compound (VII-1b)

Reaction Scheme:

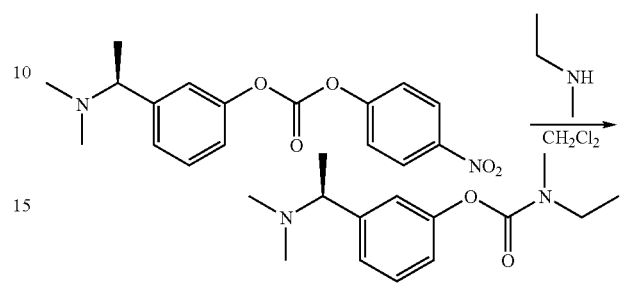

0.32 g Crude carbonate compound from Example 2 was dissolved in 5 ml dichloromethane (distilled from CaCl$_2$). 86 mg N-Ethylmethylamine was added dropwise. The yellow solution was stirred at ambient temperature. Reaction progress was monitored with HPLC.

After 3 hours, the reaction mixture was concentrated in vacuo. To the resulting yellow oil, 20 ml diethyl ether and 20 ml of a solution of hydrochloric acid (2 M) were added. The 2-phase system was stirred for 15 minutes. The acidic aqueous layer was washed with 20 ml diethyl ether.

20 ml dichloromethane was added to the aqueous layer and a solution of sodium hydroxide (2 M) was added until pH~12 was reached. The organic layer was washed with 2×20 ml water, dried (Na$_2$SO$_4$), filtered and concentrated in vacuo.

| Isolated yield: | 0.15 g (62%), yellow oil |
| --- | --- |
| HPLC: | 96.9% purity; 99.1% e.e. |

Example 4

Synthesis of the Compound (Ia) (Racemate)

Reaction Scheme:

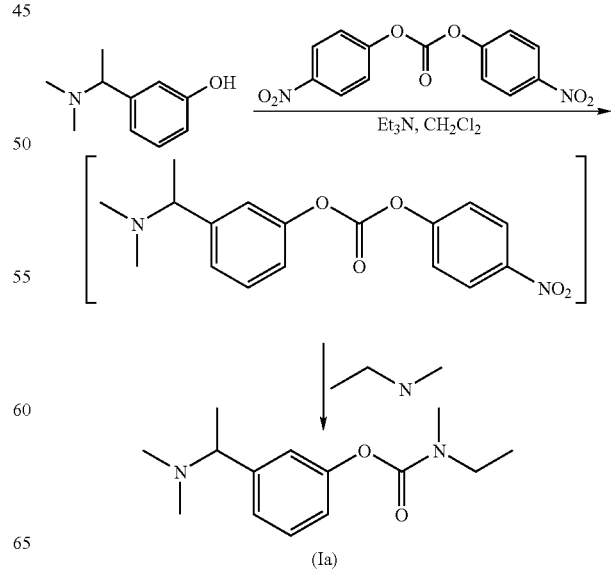

Process:

1 g 3-(1-(Dimethylamino)ethyl) phenol was dissolved in 20 ml dichloromethane (distilled from $CaCl_2$). The solution was cooled with an ice-water bath (0-5° C.). 0.92 g triethylamine was added. 2.21 g bis(4-nitrophenyl)carbonate was added. The yellow solution was stirred in an ice-water bath.

Reaction progress was monitored by HPLC. After 4 hours, 715 mg N-ethylmethylamine was added and the yellow solution was stirred for 17 hours at 4° C. The reaction mixture was allowed to warm to room temperature and was then washed with 2×20 ml water. The organic phase was concentrated in vacuo. To the resulting yellow oil, 20 ml diethyl ether and 20 ml of a solution of hydrochloric acid (2 M) were added. The 2-phase system was stirred for 15 minutes. The acidic aqueous layer was washed with 20 ml diethyl ether.

20 ml dichloromethane was added to the aqueous layer and a solution of sodium hydroxide (2 M) was added until pH~12 was reached. The organic layer was washed with 2×20 ml water, dried ($Na_2SO_4$), filtered and concentrated in vacuo.

| Isolated yield: | 1.37 g (90%), yellow oil |
| --- | --- |
| HPLC: | 98% purity |
| $^1$H-NMR: | confirmed the expected structure |

Example 5

Synthesis of the Compound (Ia)

1 g 3-(1-(Dimethylamino)ethyl) phenol was dissolved in 20 ml dichloromethane (distilled from $CaCl_2$). 0.92 g triethylamine was added. 2.21 g bis(4-nitrophenyl)carbonate was added. The yellow solution was stirred at ambient temperature.

Reaction progress was monitored by HPLC. After 2.5 hours, 715 mg N-ethylmethylamine was added dropwise and the yellow solution was stirred for 1.5 hours at ambient temperature. The reaction mixture was washed with 2×20 ml water. The organic phase was concentrated in vacuo. To the resulting yellow oil, 20 ml diethyl ether and 20 ml of a solution of hydrochloric acid (2 M) were added. The 2-phase system was stirred for 15 minutes. The acidic aqueous layer was washed with 20 ml diethyl ether.

20 ml dichloromethane was added to the aqueous layer and a solution of sodium hydroxide (2 M) was added until pH~12 was reached. The organic layer was washed with 2×20 ml water, dried ($Na_2SO_4$), filtered and concentrated in vacuo.

| Isolated yield: | 1.36 g (90%), yellow oil |
| --- | --- |
| HPLC: | 97% purity |
| $^1$H-NMR, $^{13}$CNMR: | confirmed the expected structure |

Examples 6-9

The Example 5 was repeated in the following solvents and with the following results:

TABLE 2

| Exp. code | Solvent | Reaction temperature (° C.) | Isolated yield (%) | Purity acc. to HPLC (%) |
| --- | --- | --- | --- | --- |
| Example 6 | THF | 0-5 | 80 | 96.7 |
| Example 7 | $CH_3CN$ | 0-5 | 80 | 95.7 |
| Example 8 | EtOAc | 0-5 | 66 | 93.9 |
| Example 9 | Acetone | 0-5 | 92 | 97.1 |

Example 10

Synthesis of the Compound (Ia)

0.5 g 3-(1-(Dimethylamino)ethyl) phenol was dissolved in 10 ml dichloromethane (distilled from $CaCl_2$). 1.1 g bis(4-nitrophenyl)carbonate was added. The yellow solution was stirred at ambient temperature.

Reaction progress was monitored with HPLC. After 2 hours, 358 mg N-ethylmethylamine was added dropwise and the yellow solution was stirred at ambient temperature for 16 hours. The reaction mixture was concentrated in vacuo. To the resulting yellow oil, 20 ml diethyl ether and 20 ml of a solution of hydrochloric acid (2 M) were added. The 2-phase system was stirred for 15 minutes. The acidic aqueous layer was washed with 20 ml diethyl ether.

20 ml dichloromethane was added to the aqueous layer and a solution of sodium hydroxide (2 M) was added until pH~12 was reached. The organic layer was washed with 2×20 ml water, dried ($Na_2SO_4$), filtered and concentrated in vacuo.

| Isolated yield: | 0.62 g (82%), yellow oil |
| --- | --- |
| HPLC: | 97.4% purity |

Example 11

Synthesis of the Compound (Ia)

1.0 g 3-(1-(Dimethylamino)ethyl) phenol was dissolved in 20 ml acetone. 2.21 g bis(4-nitrophenyl)carbonate was added. The yellow solution was stirred at ambient temperature.

Reaction progress was monitored with HPLC. After 1.5 hour, 537 mg N-ethylmethylamine was added dropwise and the yellow solution was stirred at ambient temperature for 1.5 hour. The reaction mixture was concentrated in vacuo. To the resulting yellow oil, 20 ml t-butylmethyl ether and 20 ml of a solution of hydrochloric acid (2 M) were added. The 2-phase system was stirred for 15 minutes. The acidic aqueous layer was washed with 20 ml t-butylmethyl ether.

20 ml t-Butylmethyl ether was added to the aqueous layer and a solution of sodium hydroxide (2 M) was added until pH~12 was reached. The organic layer was washed with 2×20 ml water, dried ($Na_2SO_4$), filtered and concentrated in vacuo.

| Isolated yield: | 1.34 g (88%), yellow oil |
| --- | --- |
| HPLC: | 95.6% purity |

Example 12

Synthesis of Rivastigmine (Ib)

Reaction scheme:

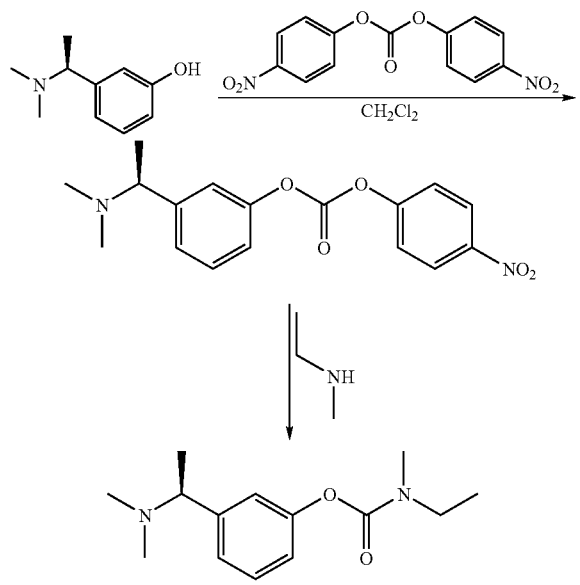

0.5 g (S)-3-(1-(Dimethylamino)ethyl) phenol was dissolved in 10 ml dichloromethane (distilled from CaCl$_2$). 1.1 g bis(4-nitrophenyl)carbonate was added. The yellow solution was stirred at ambient temperature.

Reaction progress was monitored with HPLC. After 1.5 hour, 357 mg N-ethylmethylamine was added dropwise and the yellow solution was stirred at ambient temperature for 2.5 hours. The reaction mixture was concentrated in vacuo. To the resulting yellow oil, 10 ml diethyl ether and 10 ml of a solution of hydrochloric acid (2 M) were added. The 2-phase system was stirred for 10 minutes. The acidic aqueous layer was washed with 10 ml diethyl ether.

10 ml dichloromethane was added to the aqueous layer and a solution of sodium hydroxide (2 M) was added until pH~12 was reached. The organic layer was washed with 2×10 ml water, dried (Na$_2$SO$_4$), filtered and concentrated in vacuo.

| Isolated yield: | 0.58 g (76%), yellow oil |
|---|---|
| HPLC: | 94% purity; |

Example 13

Synthesis of Rivastigmine 0.5 g (S)-3-(1-(Dimethylamino)ethyl) phenol was dissolved in 10 ml dichloromethane (distilled from CaCl$_2$). 1.11 g bis(4-nitrophenyl)carbonate was added. The yellow solution was stirred at ambient temperature.

Reaction progress was monitored by HPLC. After 1.5 hours, 357 mg N-ethylmethylamine was added dropwise and the yellow solution was stirred for 2.5 hours at ambient temperature. The reaction mixture was concentrated in vacuo. To the resulting yellow. oil, 10 ml diethyl ether and 10 ml of a solution of hydrochloric acid (2 M) were added. The 2-phase system was stirred for 10 minutes. The acidic aqueous layer was washed with 10 ml diethyl ether.

20 ml dichloromethane was added to the aqueous layer and a solution of sodium hydroxide (2 M) was added until pH~12 was reached. The organic layer was washed with 2×10 ml water, dried (Na$_2$SO$_4$), filtered and concentrated in vacuo.

| Isolated yield: | 0.58 g (76%), yellow oil |
|---|---|
| HPLC: | 93.92% purity, 99% ee |

Each of the patents, patent applications, and journal articles mentioned above are incorporated herein by reference. The invention having been described it will be obvious that the same may be varied in many ways and all such modifications are contemplated as being within the scope of the invention as defined by the following claims.

We claim:
1. A process, which comprises:
   (a) reacting a compound of formula (II)

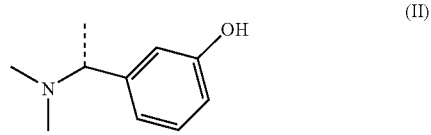

with bis(p-nitrophenyl)carbonate of formula (IX)

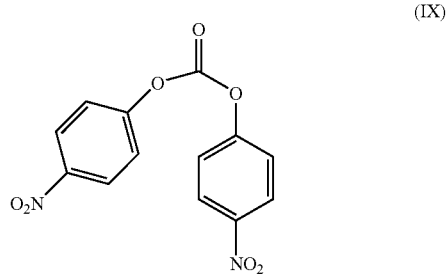

to form an intermediate and
(b) reacting said intermediate with ethylmethylamine of formula (III)

to form a compound of formula (I)

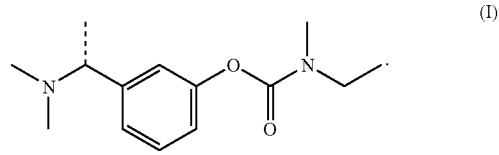

2. The process according to claim 1, wherein said compound of formula (II) is a compound of formula (IIb)

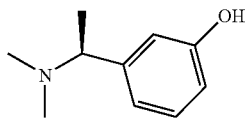
(IIb)

and said compound of formula (I) being formed is a compound of formula (Ib)

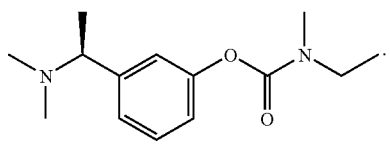
(Ib)

3. The process according to claim 1, wherein said compound of formula (II) is a compound of formula (IIa)

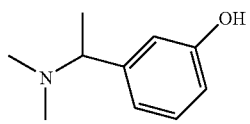
(IIa)

and said compound of formula (I) being formed is a racemic mixture of compounds; and which process further comprises resolving said racemic mixture of compounds of formula (I) to obtain substantially the compound of formula (Ib)

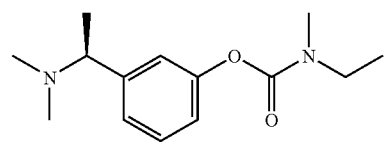
(Ib)

or a salt thereof.

4. The process according to claim 1, wherein step (a) is carried out at a temperature between −20 to 50° C.

5. The process according to claim 4, wherein said temperature in step (a) is within the range from 0 to 30° C.

6. The process of claim 1, wherein step (a) is carried out in a solvent selected from the group consisting of a C1-C10 ether, a C5-C8 cyclic ether, a C2-C10 aliphatic ester, a C2-C8 aliphatic nitrile, an amide, a sulfoxide, a ketone, a C5-C10 hydrocarbon, a C1-C8 chlorinated hydrocarbon, and mixtures thereof.

7. The process according to claim 6, wherein said solvent used in step (a) is selected from the group consisting of methyl tert. butyl ether, tetrahydrofuran, ethyl acetate, acetonitrile, dimethylformamide, dimethyl sulfoxide, acetone, hexane, toluene, chloroform, dichloromethane, and mixtures thereof.

8. The process according to claim 1, wherein the reaction in step (a) is carried out in the presence of a base.

9. The process according to claim 8, wherein said base is an organic base.

10. The process according to claim 6, wherein step (a) and step (b) are carried out as a one pot process.

11. The process according to claim 10, wherein a solvent used for steps (a) and (b) is selected from the group consisting of methyl tert. butyl ether, tetrahydrofuran, ethyl acetate, acetonitrile, dimethylformamide, dimethyl sulfoxide, acetone, hexane, toluene, chloroform, dichloromethane, and mixtures thereof.

12. The process according to claim 10, wherein step (b) is carried out at a temperature between −20 to 50° C. and in the presence of an organic base.

13. The process according to claim 12, wherein the reaction temperature in step (b) is from 0 to 30° C.

14. The process according to claim 1, which further comprises isolating the compound of formula (1) as the L-hydrogentartrate salt of rivastigmine.

15. A process for making rivastigmine, which comprises
a) reacting a compound of formula (IIb) with a compound of formula (IX)

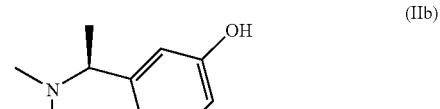
(IIb)

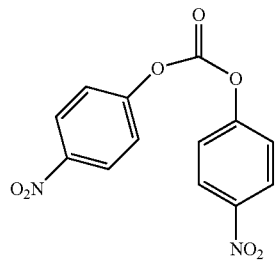
(IX)

in an inert solvent at a temperature within the range of −20° C. to 50° C. to form a compound of formula (VII-1b)

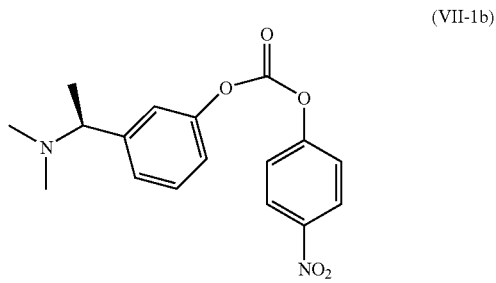
(VII-1b)

and (b) reacting said compound of formula (VII-1b) with a compound of formula (III)

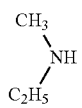

in an inert solvent at a temperature within the range of −20° C. to 50° C. to form a compound of formula (Ib)

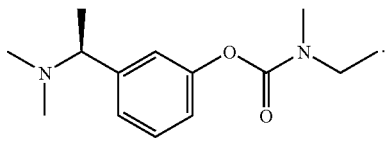 (Ib)

16. The process according to claim 15, which further comprises isolating said compound of formula (VII-1b) before carrying out said reaction in step (b).

17. The process according to claim 15, which further comprises isolating said compound of formula (Ib) or a salt thereof.

18. The process according to claim 15, wherein said solvent in steps (a) and (b) is the same and is selected from the group consisting of methyl tert. butyl ether, tetrahydrofuran, ethyl acetate, acetonitrile, dimethylformamide, dimethyl sulfoxide, acetone, hexane, toluene, chloroform, dichloromethane, and mixtures thereof.

19. The process according to claim 18, wherein said reactions in steps (a) and (b) are each conducted in the presence of an organic base.

20. The process according to claim 19, wherein each of steps (a) and (b) is carried out at a temperature within the range of 0 to 30° C.

* * * * *